(12) United States Patent
Karamchedu et al.

(10) Patent No.: US 8,332,239 B2
(45) Date of Patent: Dec. 11, 2012

(54) AUTOMATIC PATIENT RECORD UPDATE ENABLED CLINICAL MESSAGING

(75) Inventors: Murali M. Karamchedu, Beaverton, OR (US); Jeffrey B. Sponaugle, Hillsboro, OR (US); James Vincent Coppa, Portland, OR (US)

(73) Assignee: Kryptiq Corporation, Hillsboro, OR (US)

( * ) Notice: Subject to any disclaimer, the term of this patent is extended or adjusted under 35 U.S.C. 154(b) by 1825 days.

(21) Appl. No.: 11/193,316

(22) Filed: Jul. 29, 2005

(65) Prior Publication Data

US 2007/0027717 A1 Feb. 1, 2007

(51) Int. Cl.
*A61B 5/00* (2006.01)

(52) U.S. Cl. ............ 705/3; 705/2; 600/300; 340/539.12

(58) Field of Classification Search ............... 340/573.1; 705/2, 3; 707/10, 104.1; 709/206; 1/1
See application file for complete search history.

(56) References Cited

U.S. PATENT DOCUMENTS

| | | | | |
|---|---|---|---|---|
| 5,930,759 | A * | 7/1999 | Moore et al. | 705/2 |
| 6,915,265 | B1 * | 7/2005 | Johnson | 705/2 |
| 6,978,268 | B2 * | 12/2005 | Thomas et al. | 707/10 |
| 7,034,691 | B1 * | 4/2006 | Rapaport et al. | 340/573.1 |
| 7,295,988 | B1 * | 11/2007 | Reeves | 705/3 |
| 2002/0103811 | A1 * | 8/2002 | Fankhauser et al. | 707/104.1 |
| 2003/0233252 | A1 * | 12/2003 | Haskell et al. | 705/2 |
| 2004/0153515 | A1 * | 8/2004 | Touboul et al. | 709/206 |
| 2004/0236602 | A1 * | 11/2004 | Greene | 705/2 |
| 2004/0267572 | A1 * | 12/2004 | Emery et al. | 705/2 |
| 2005/0144044 | A1 * | 6/2005 | Godschall et al. | 705/3 |
| 2005/0187973 | A1 * | 8/2005 | Brychell et al. | 707/104.1 |

OTHER PUBLICATIONS

Google patents search result, Sep. 4, 2012.*

* cited by examiner

*Primary Examiner* — Dilek B Cobanoglu
(74) *Attorney, Agent, or Firm* — Schwabe, Williamson & Wyatt, P.C.

(57) ABSTRACT

Embodiments of the present invention provide methods and apparatuses for automatic patient record creation for messaging. Embodiments provide messaging systems, devices and methods for electronic clinical messaging with transmission of a record or data from a sender to a recipient and automatic creation of patient records upon receipt by a recipient.

8 Claims, 3 Drawing Sheets

US 8,332,239 B2

AUTOMATIC PATIENT RECORD UPDATE ENABLED CLINICAL MESSAGING

TECHNICAL FIELD

Embodiments of the present invention relate to the field of data processing, and, in particular, to methods and apparatuses for automatic patient record update enabled messaging applications.

BACKGROUND

With advances in integrated circuit, microprocessor, networking and communication technologies, an increasing number of devices, in particular, digital computing devices, are being interconnected. This increased interconnectivity of computing devices has laid the groundwork for a communication infrastructure particularly well suited for electronic communications between such computing devices. More specifically, the increased interconnectivity of computing devices has led to the near ubiquitous adoption of electronic mail (email) as a standard mode of communication.

In the past, electronic mail communications were limited to the exchange of text-based messages between a relatively small populous. Over time, however, email applications and associated communications protocols have become increasingly sophisticated enabling more complex messages to be exchanged between larger numbers of individuals. For example, in addition to enabling the exchange of simple text-messages, many modern day email clients allow users to exchange complex, multipart MIME (Multipurpose Internet Mail Extensions) encoded files as well as a wide variety of binary attachments.

BRIEF DESCRIPTION OF THE DRAWINGS

Embodiments of the present invention will be readily understood by the following detailed description in conjunction with the accompanying drawings. To facilitate this description, like reference numerals designate like structural elements. Embodiments of the invention are illustrated by way of example and not by way of limitation in the figures of the accompanying drawings.

DETAILED DESCRIPTION OF EMBODIMENTS OF THE INVENTION

Figure 1:
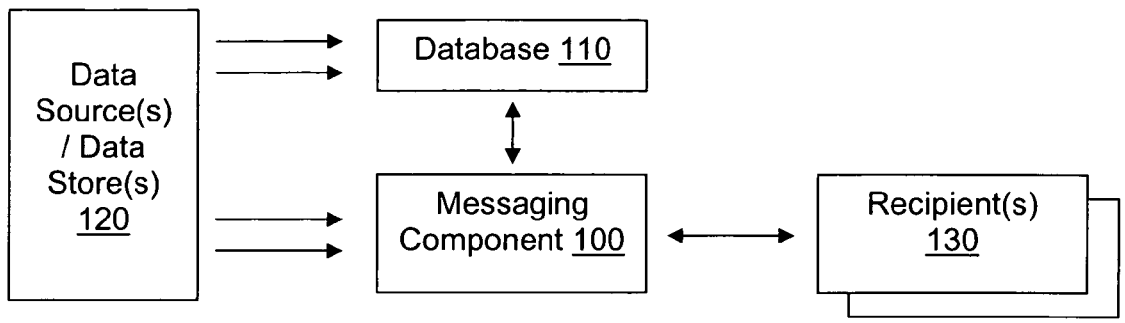
FIG. 1 illustrates a messaging system in accordance with an embodiment of the present invention.

In the following detailed description, reference is made to the accompanying drawings which form a part hereof wherein like numerals designate like parts throughout, and in which is shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

The description is presented, in part, in terms of operations performed by a processor based device, using terms such as receiving, determining, rendering, displaying and the like, consistent with the manner employed by those skilled in the art. Quantities may take the form of electrical, magnetic, or optical signals capable of being stored, transferred, combined, and/or otherwise manipulated through mechanical, electrical and/or optical components of a processor based device.

Various operations may be described as multiple discrete steps in turn, in a manner that may be helpful in understanding embodiments of the present invention; however, the order of description should not be construed to imply that these operations are order dependent.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In an embodiment of the present invention, a storage server may be employed to facilitate users of client devices in sending, for example, partially or fully secure electronic messages to one or more recipients. Similarly, a user (i.e. "sender") of a messaging client (i.e. "sending client") incorporated with the teachings of the present invention may be able to compose an electronic message to be delivered to one or more recipients, for example, in either a fully secured or partially secured manner. Furthermore, in an embodiment of the present invention, the sender may employ one or more predefined or custom generated forms as a basis for the electronic message and/or a message delivery notification designed to alert the recipient(s) of the availability of the electronic message and any possible attachments. In an embodiment of the present invention, a sender may require certain inputs to be entered by an intended recipient of a secure message (whether fully or partially secure), such as passwords or answers to survey questions, before the recipient may be provided with the secure message. In an embodiment of the present invention, the sender may elect to have the content of the delivered message be dependent upon the inputs provided by the recipient prior to delivery of the message. In an embodiment of the present invention, a split encryption key methodology may be utilized in which secure messages or portions of messages may be stored in an encrypted form on the storage server in conjunction with only a portion of the access information necessary to access a given secure message. Other encryption methods may be employed in embodiments of the present invention depending on the desired application.

In the following description including the claims, unless further particularized or otherwise noted, the term "message" is intended to broadly refer to electronic messages, email messages, attachments and/or data files in whole or in part, whether or not they comprise a text, binary, or otherwise encoded form, and whether or not they are transmitted via Simple Mail Transport Protocol (SMTP), HTTP, file transfer protocol (FTP), trivial file transfer protocol (TFTP), or otherwise.

FIG. 1 is a block diagram illustrating a messaging system in accordance with an embodiment of the present invention. In an embodiment of the present invention, messaging component 100 may be equipped to facilitate the composition, for example by a user, and transmission of messages and/or data to one or more recipients 130. In an embodiment of the present invention, messaging component 100 may be equipped with secure messaging services including message notification and form generation logic to facilitate the exchange of secure messages. Recipient(s) 130 may represent one or more computing devices equipped with a generic user agent to receive and transmit messages.

In an embodiment of the present invention, messaging component 100 may access a variety of documents for attachment in one or more messages directly from various data source(s) and/or data store(s) 120, and/or from a database 110. Database 110 may additionally contain data in a variety of suitable formats and/or structures. Database 110 may also point or link to and/or receive data from various data source(s) and/or data store(s) 120.

In an exemplary embodiment of the present invention, a messaging component 100 may be clinical messaging software for use by health care providers, such as physicians, nurses, administration staff, etc. A recipient may be, for example, a patient or another provider. In an embodiment of the present invention, a suitable database may be a clinical database or an electronic records system, such as an electronic health or patient records (EHR) system, that provides for integration with other data sources and/or data stores. Thus, according to an embodiment of the present invention, a clinical messaging component may be integrated or coupled with an electronic health/patient records system, and linked with associated sources and/or stores of data, documents, etc. such that the clinical messaging component may package the data in a clinical message to be delivered to a recipient. According to embodiments of the present invention, the term "clinical" should be given broad interpretation as related to health or medical care.

In an embodiment of the present invention, providers may send referrals and/or patient records electronically via secure messaging. Clinical data, including, for example, patient data, such as chart summaries, laboratory reports, xrays, etc., may be attached to an electronic message, for example, from an electronic health/patient records system, thus saving time and money, for the sender and recipient, by eliminating or reducing manual and paper-based processing including printing, faxing, scanning, and follow-up phone calls.

With multiple discrete electronic records systems, for example multiple EHRs, running, it may be difficult to share data between the various EHRs. Thus, embodiments of the present invention may facilitate interconnection of various EHRs and/or various locations of care. A location of care may refer to a geographic location, or to an individual provider, a particular provider network, and/or practice groups within a provider network. Embodiments of the present invention may interconnect multiple EHR systems, whether the systems use the same or different applications, and whether the systems are located at the same or different locations of care.

Figure 2:
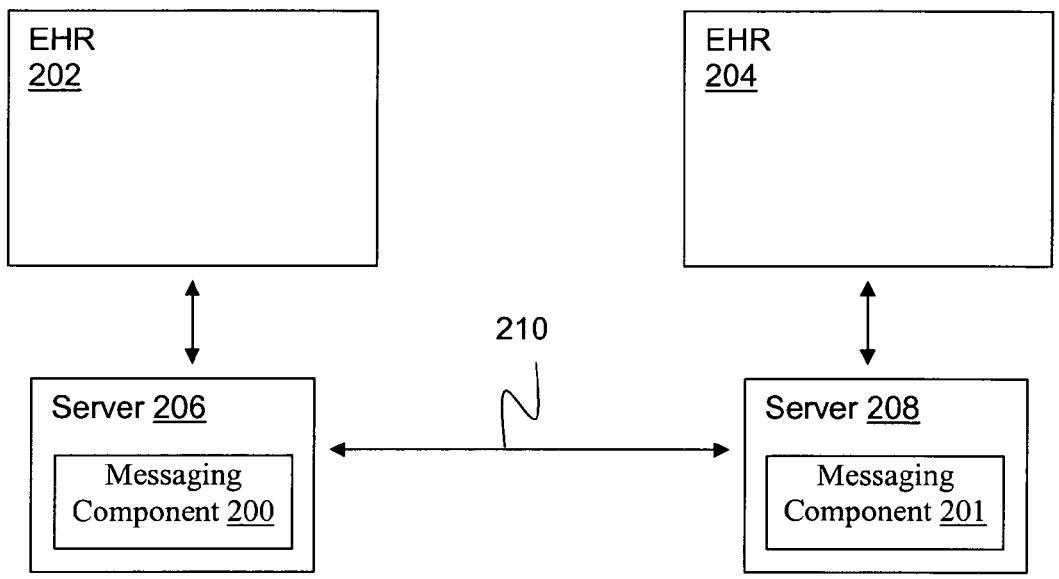
FIG. 2 illustrates a number of EHR systems linked by messaging systems in accordance with an embodiment of the present invention.

An embodiment of the present invention provides a communication platform that links different servers with messaging components together, and thus different EHRs together, for the purpose of exchanging clinical data. FIG. 2 illustrates a communication link between two servers 206 and 208 having messaging components 200, 201 according to an embodiment of the present invention. For the purposes of this illustration, server 206 may be the sending server and server 208 may be the recipient server. Messaging component 200 of server 206 may communicate with EHR 202 and other applications, etc. In an embodiment of the present invention, data from EHR 202 may be sent (210) in the form of a message through server 206, using messaging component 200, to messaging component 201. In an embodiment of the present invention, data may be sent (210) between servers 206 and 208, using messaging components 200, 201, for example, as an SMTP, SMTP-like, or MIME message. In an embodiment of the present invention, in server 206, data may be decomposed by messaging component 200, and then the decomposed data may be reconstituted by server 208, using messaging component 201. Server 208, or more specifically, messaging component 201, may then push the message and/or data to EHR 204.

In an embodiment of the present invention, for example, a primary care physician (PCP) may be linked to a specialist to effect a patient referral. A message may be created in and sent out through the PCP's messaging component (optionally including data records and/or documents in the PCP's EHR), as an SMTP, SMTP-like, or MIME message. The specialist's messaging component may receive the message and then push the data record and/or document into the specialist's EHR. In an embodiment of the present invention, a specialist may store the received data locally in the specialist's EHR. In an embodiment of the present invention, the received data may be automatically employed to update the patient's records in the recipient specialist's EHR, if the patient is an existing patient of the recipient specialist. In an embodiment of the present invention, a new patient file or record may be automatically generated in the recipient's EHR from the data provided in the message sent by the sender primary provider, if the patient is not an existing patient of the recipient specialist. Note that the terms provider and specialist as used herein refer to the provider and specialist themselves, as well as those agents (e.g. their staffs) acting on behalf of the provider and/or specialist.

Figure 3:
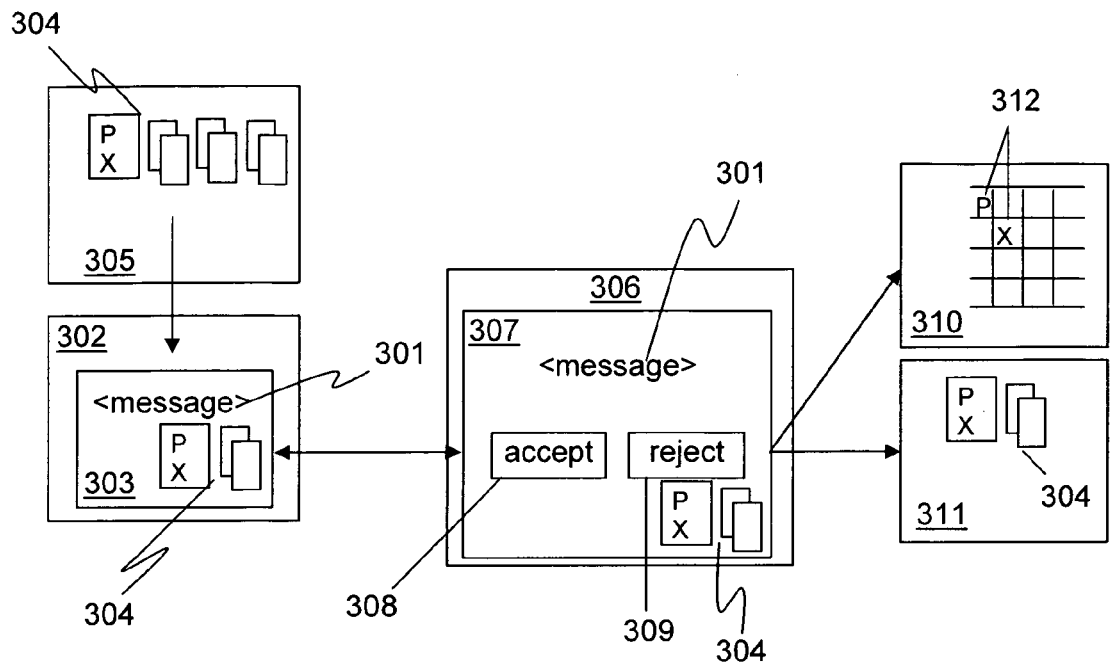
FIG. 3 illustrates a clinical messaging scheme for transmitting and receiving a message in accordance with an embodiment of the present invention.

FIG. 3 illustrates a message attachment scheme for transmitting and receiving a message 301 with attachments in accordance with an embodiment of the present invention. The message attachment scheme may be practiced together with the earlier described messaging scheme. A message 301 may be generated in sender's messaging component 302. In an embodiment of the present invention as shown in FIG. 3, a graphical user interface 303 may be provided to facilitate the selection and attachment of various documents 304 from database, data source or data store 305 (hereafter database 305) to electronic message 301.

In an embodiment of the present invention, documents 304 may be heterogeneous documents. For the purposes of various embodiments of the present invention, the term "heterogeneous documents" refers to documents that differ, for example, in form, format, and/or data structure. For example, embodiments of the present invention enable and facilitate the use of heterogeneous documents in messaging and thus do not force the use of a common data structure or format, such as using only PDF documents, in a message.

In an embodiment of the present invention, database 305 may store data in a structured format, such as structured patient data as in a patient's medical records. For example, a patient's medical records may include physician's notes, diagnostic test results, laboratory reports, etc. In such an embodiment, users may include physicians, administrators, nurses, medical office staff, etc.

According to an embodiment of the present invention, a graphical user interface 303 may run as part of messaging component 302. Messaging component 302 may be a standalone messaging component or integrated with an application or a suite of applications. In an embodiment of the present invention, messaging component 302 may be a clinical messaging component and/or database 305 may be a clinical database.

In an embodiment of the present invention, a user may access graphical user interface (GUI) 303 and, from GUI 303, may create an electronic message 301, and/or select documents 304 for attachment to electronic message 301.

In an embodiment of the present invention, an electronic message 301 may be sent to a recipient via server to server communication, or other communication mechanisms. For example, in an embodiment of the present invention, when a sender transmits a message using a messaging component, the message contents may be encrypted and stored on a server inside the firewall of the sender. The recipient may receive a notification that contains a link to the secure message, which may initiate a secure connection to the server, for example, via a web browser. In an embodiment of the present invention, recipients may be authenticated before being allowed to view the message. Once accessed, the message and any attachments may be stored to the recipient's EHR, or printed, if desired.

In an embodiment of the present invention, a recipient's messaging component 306 may receive a message 301 with attached documents 304, as represented in GUI 307. A recipient may access data and/or documents 304 attached to a message 301, for example, by clicking on a link or icon in message 301. In an embodiment of the present invention, messaging component 306 may provide message 301 as received by a recipient with a button or icon for the recipient to indicate whether the recipient accepts (308) or rejects (309) the data and/or patient identified by the contents of message 301.

In an embodiment of the present invention, if a recipient rejects (309) the data and/or patient identified by the contents of message 301, a return message may be manually or automatically generated to report to the sender that the message, for example a patient referral, has been rejected.

In an embodiment of the present invention, if a recipient accepts (308) the data and/or patient identified by the contents of message 301, the recipient's messaging component 306 may then determine whether the identified patient is a new patient or an existing patient. In an embodiment of the present invention, if the patient is an existing patient of the recipient, data may be manually or automatically associated with the record established previously for that patient. In an embodiment of the present invention, if the patient is a new patient, logic may be manually or automatically initiated based on that determination to extract documents and/or data from the message and populate a database and/or data store 310, 311. Documents 304 may be stored in a data store or database 311, or, in an embodiment of the present invention, data may be extracted from message 301 or from documents 304 (such as exemplary data elements P and X shown in documents 304) to populate a database 310.

Thus, in embodiments of the present invention, documents may be stored in their entirety and/or data may be extracted from the documents, or from the contents of the message, and may be used to populate a database. In embodiments of the present invention, data may be encoded using various suitable languages, such as XML, to facilitate communication between the sender and recipient and to ensure the data is properly routed and/or stored.

In an embodiment of the present invention, a message may contain an identifier in the subject line or in the body of the message to identify the specific record, data, and/or patient being transmitted or referred. Furthermore, information regarding the current context of an application running at the sender's end may provide a tag to the message to identify the particular application context, for example, the particular patient record being viewed and/or processed by the sender when the message is generated or sent.

In accordance with an embodiment of the present invention, a mechanism for associating documents with each other may also be used to provide an embedded document identifier in each document or data element prior to attaching and/or storing data or a document in a database or data store, such as an EHR. Document inter-relation may further assist in proper storage and auto-creation and/or auto-population of a database by providing a further mechanism to identify a document and its relation to other documents or data records.

Whether operating in a messaging component, such as a clinical messaging component, or in a database or data store, an embodiment of the present invention provides a method to relate various stored documents and/or documents attached in an electronic message with each other. Documents may be related to each other in a variety of ways, including establishing a cross-related document nomenclature, storing related documents in files or in a structured hierarchy, etc. In an embodiment of the present invention, when a document is stored or attached in an electronic message, the document may be examined to determine whether it has been embedded with an identifier and associated with an entity (e.g. a patient). If a document has an embedded identifier, the identifier may be compared to the identifiers in the record and used to ensure that the document is routed and/or stored in the proper location in the electronic records.

If a document has not been associated with an entity, an identifier identifying the entity may be injected into the document. Such an identifier provides for a mechanism to relate multiple documents to each other, as well as document search and discovery functions based on the identifier.

If a document has not been associated with an entity, an identifier may be embedded in the created document, for example, in the document header, in a package header, and/or as metadata or a metadata tag. An identifier may be unique to a document, or, in an embodiment of the present invention, may be an identifier that is unique to a set of documents to provide inter-relatability of those documents. For example, in an embodiment of the present invention, documents may be individual components of a patient's medical chart and an identifier may be a patient identifier.

In various embodiments, an identifier may be derived from a current context of an application, e.g. an application having the messaging component integrated. More specifically, in embodiments in which the messaging component is integrated with a clinical application, the identifier may be the current patient identifier of the records and/or data being viewed and/or processed.

In an embodiment of the present invention, a trail of data may be created and returned to the sender to track the transmission of data and show when and by whom a message is sent, received, viewed and/or processed, for example, when a recipient downloads or prints a message or an attachment. For the purposes of embodiments of the present invention, a trail of data may be referred to as an audit trail. An audit trail may be used to assist a provider, for example, to further reduce unnecessary follow-up communications and also in complying with specific regulations under HIPAA.

Figure 4:
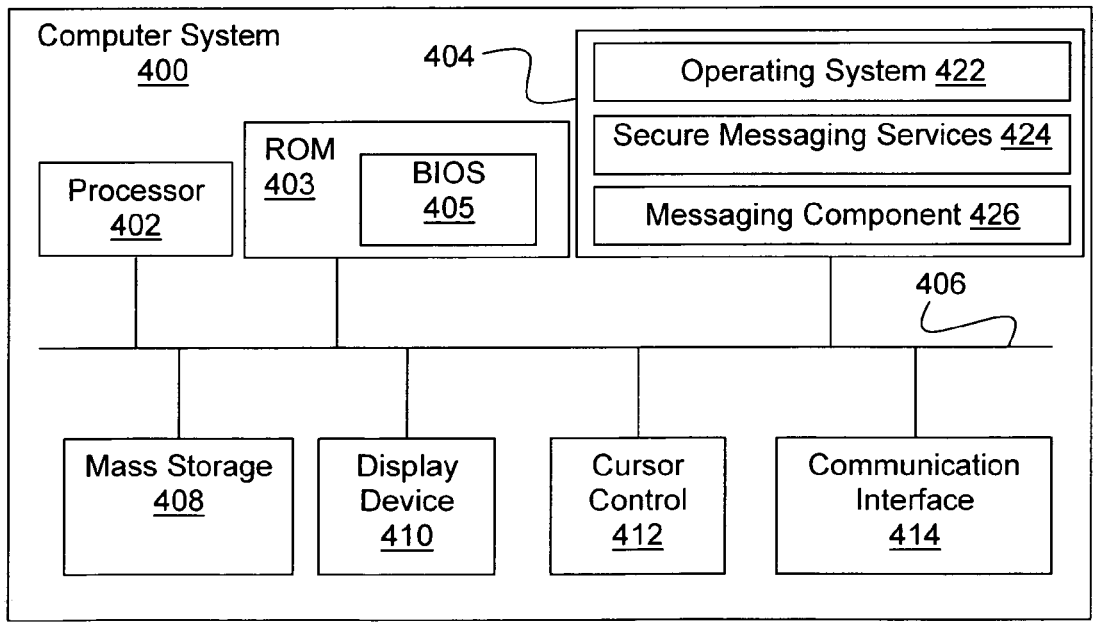
FIG. 4 illustrates an exemplary computer system suitable for use as a sending or receiving client or server in accordance with embodiments of the present invention.

FIG. 4 illustrates an exemplary computer system suitable for use as a sending or recipient client or server in accordance with embodiments of the present invention. As shown, example computer system 400 includes processor 402, ROM 403 including basic input/output system (BIOS) 405, and system memory 404 coupled to each other via "bus" 406. Also coupled to "bus" 406 are non-volatile mass storage 408, display device 410, cursor control device 412 and communication interface 414. During operation, memory 404 may also include working copies of operating system 422, messaging component 426, and (client side of) secure messaging services 424. In various embodiments, memory 404 may also include one or more applications (not shown), with which messaging component 426 is integrated or coupled. In the case of the sending client, secure messaging services 424 may include message notification and form generation logic in accordance with embodiments of the present invention to facilitate the exchange of secure messages between a sending client, storage server, and one or more recipients. In the case of a storage server, messaging services 424 facilitate storage and encryption of messages/data on behalf of a sending client, and the generation of one or more encryption keys to facilitate recipient access to the encrypted messages/data. In other embodiments, system 400 may also include an EHR system.

Figure 5:
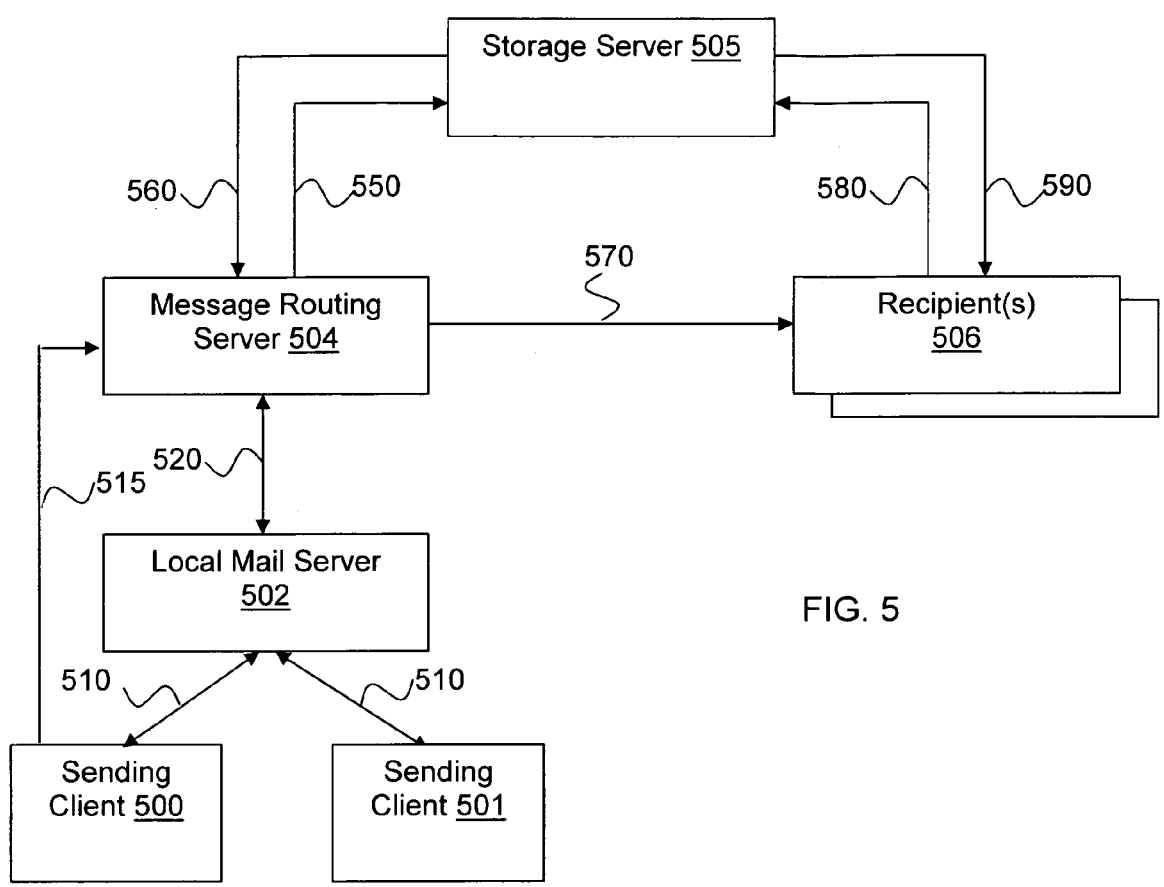
FIG. 5 illustrates an enterprise based secure messaging system including various logical device interactions in accordance with an embodiment of the present invention.

In accordance with an embodiment of the present invention, an enterprise based secure messaging system may be provided. The enterprise secure messaging system may be practiced in conjunction with the earlier described messaging scheme and/or message attachment scheme. FIG. 5 illustrates an enterprise based secure messaging system including various logical device interactions, in accordance with an embodiment of the present invention. In accordance with an embodiment of the present invention, local mail server 502 represents a server equipped with electronic mail services, such as those provided by Exchange from Microsoft Corporation or Domino from IBM Corporation, to receive outgoing message transmission requests from clients 500 and 501, to receive incoming messages to be delivered to clients 500 and 501, and to temporarily store or queue both the outgoing and incoming messages until such time that the message destination domains/devices may be determined and contacted.

Message routing server 504 represents a server that may route mail traffic from local mail server 502 (and sending clients 500 and 501) to storage server 505 and recipients 506, much like a mail gateway. In an embodiment of the present invention, outgoing messages from local mail server 502 are first directed to message routing server 504 before they are delivered to storage server 505 and/or recipients 506.

In an embodiment of the present invention, a sender corresponding to either sending client 500 or 501 may compose an electronic message addressed to one or more recipients 506, that may first be delivered to local mail server 502 (510). In an embodiment of the present invention, local mail server 502 may unconditionally transmit (e.g. via redirection or forwarding) messages it receives to message routing server 504, whereas in another embodiment of the present invention, mail server 502 may transmit messages to message routing server 504 based upon whether or not the message is to be stored and/or delivered in a secure manner by storage server 505. In an embodiment of the present invention, sending client 500/501 may transmit an HTTP-based request directly (e.g. via a browser application) to message routing server 504 identifying the message to be securely stored and delivered, effectively bypassing local mail server 502 (515).

In an embodiment of the present invention, message routing server 504 may determine (based, for example, upon a variety of criteria such as source or destination address, content of the message, size of the message, etc.) whether a particular message is to be stored and delivered by storage server 505 in a secure manner. In an embodiment of the present invention, an SMTP or HTTP-based message may include an identifier (e.g. in an associated header field) that indicates to message routing server 504 whether the message is to be securely stored and delivered in accordance with the teachings of embodiments of the present invention.

If it is determined that an identified message is to be securely stored and/or delivered, message routing server 504 may transmit a request to storage server 505 to store the identified message (or portion of a message) securely (550). In an embodiment of the present invention, in response to the request of message routing server 504, storage server 505 may securely store the identified message and generate access data associated with the securely stored message. In an embodiment of the present invention, the access data may be represented by an access token that may include just the access data or supplemental information in addition to the access data. In an embodiment of the present invention, storage server 505 may encrypt the message, for example, using a split encryption key having two or more key portions, with storage server 505 retaining a first key portion and transmitting a second key portion to the sending client. In other embodiments of the present invention, however, storage server 505 may employ other encryption methods or other means of securely storing the message besides encryption.

Once generated, the access token may be returned to message routing server 504 by storage server 505 (560). In an embodiment of the present invention, storage server 505 may combine/integrate the access token with a message notification and transmit the integrated message notification to message routing server 504. In another embodiment of the present invention, storage server 505 may transmit the access token to message routing server 504 where message routing server 504 integrates the access token with a message notification. In various embodiments of the present invention, the message notification may be selected from one or more predefined notifications or it may be dynamically or manually generated by storage server 505 and/or message routing server 504. In an embodiment of the present invention, where multiple such message routing servers are utilized by various subsidiaries of a parent company for example, each message routing server may be configured to generate subsidiary-specific notifications notwithstanding that the message routing servers are each associated with the same storage server.

Once the access token is returned to message routing server 504, message routing server 504 may transmit the integrated notification to one or more of recipients 506 to facilitate recipient access to the message (570). In an embodiment of the present invention, message notifications may be delivered from message routing server 504 to one or more recipients 506 in the form of electronic mail messages using, for example, an email based communications protocol such as SMTP or X.400. Once a recipient has received a message notification in, for example, their email inbox, the recipient may open and view the message notification as they would with any other email message. In an embodiment of the present invention, the recipient may utilize a user input device such as a mouse to select a hyperlink or one or more controls incorporated within the notification to initiate retrieval of one or more corresponding secure messages stored by storage server 505. In an embodiment of the present invention, the token may be submitted to storage server 505 by one or more of recipients 506 in response to recipient input (580).

In response to receiving the access token from the one or more recipients 506, storage server 505 may then transmit the corresponding secure message (or a portion thereof) to one or more indicated recipients 506 (590). In an embodiment of the present invention, communications between message routing server 504 and storage server 505, as well as communications between recipients 506 and storage server 505, may occur in accordance with a first communication protocol such as HTTP, whereas communications between message routing server 504 and recipients 506 may occur in accordance with a second communication protocol such as SMTP.

In an embodiment of the present invention, in addition to storage server 505 returning the access token to message routing server 504 (560), storage server 505 may further return one or more control parameters or instructions to message routing server 504 to indicate whether any post-processing in association with the message may be performed. In an embodiment of the present invention, storage server 505 may return one or more control parameters or instructions to message routing server 504 to cause message routing server (e.g. via local mail server 502 or directly) to return a message to sending client 500/501 that may include an access token to facilitate client 500/501 in accessing information as to the status of the corresponding message. In an embodiment of the present invention, message routing server 504 may return a message identifier and the first encryption key portion to the sending client 500/501 for use, for example, by the sender in obtaining log information about the associated message, such as whether a recipient has read the message or forwarded the message to another recipient.

In various embodiments, various aspects of the present invention may be implemented in discrete hardware or firmware. For example, one or more application specific integrated circuits (ASICs) may be programmed with one or more of the above-described functions of the embodiments of the present invention. In another example, one or more functions of the embodiments of the present invention may be implemented in one or more ASICs on additional circuit boards and the circuit boards may be inserted into the computer(s) described above. In another embodiment of the present invention, programmable gate arrays may be used to implement one or more functions of embodiments of the present invention. In another embodiment of the present invention, a combination of hardware and software may be used to implement one or more functions of embodiments of the present invention.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A computer implemented method, comprising:
    facilitating a health care provider message sender, by a clinical messaging component operating on a computing device, in composing a clinical email message about a patient, to be transmitted to another health care provider, wherein facilitating includes:
        facilitating the message sender in retrieving a health care related document from a data source or store for inclusion as an attachment to the clinical email message;
        determining whether the document has an embedded patient identifier associating the document with the patient; and
        embedding the patient identifier of the patient into the document to associate the document with the patient in response to the document having been determined to not have an embedded patient identifier associating the document with the patient; and
        transmitting the clinical email message with the document having the embedded patient identifier attached, on behalf of the health care provider message sender, by the clinical messaging component, to the other health care provider.

2. The method of claim 1, wherein the data source or store comprises a health or patient records system.

3. The method of claim 1, wherein transmitting the clinical message comprises transmitting the clinical message and the attached document with the embedded patient identifier as a Simple Mail Transfer Protocol (SMTP) or Multipurpose Internet Mail Extensions (MIME) message.

4. A computer implemented method, comprising:
    receiving, by a clinical messaging component operating on a computing device associated with a health care provider, a clinical email message sent by another health care provider, wherein the clinical email message includes an attached document having an embedded patient identifier identifying a patient associated with the attached document;
    determining, by the clinical messaging component, using the patient identifier, whether the patient is a new patient to the health care provider;
    in response to determining that the patient is a new patient to the health care provider, automatically causing a health or patient records system associated with the health care provider, by the clinical messaging component, to create a new patient record in the health or patient records system for the patient; and
    automatically causing the health or patient records system, by the clinical messaging component, to store and associate the attached document with the new patient record.

5. The method of claim 4, further comprising automatically causing the health or patient records system, by the clinical messaging component, to update the new patient record with content of the clinical email message.

6. The method of claim 4, further comprising automatically creating, by the clinical messaging component, an audit trail for the creation of the new patient record, and automatically transmitting, by the clinical messaging component, the audit trail for the creation of the new patient record to the other health care provider who sent the clinical email message.

7. A computer implemented method, comprising:
    receiving, by a clinical messaging component operating on a computing device associated with a health care provider, a clinical email message sent by another health care provider, wherein the clinical email message includes an attached document having an embedded patient identifier identifying a patient associated with the attached document; and
    automatically processing the clinical email message, by the clinical messaging component in conjunction with a health or patient records system of the health care provider,
    wherein automatically processing includes automatically:
        creating an audit trail to show when and by whom the clinical email message is received or viewed; and
    transmitting the audit trail to the other health care provider who sent the clinical email message.

8. The method of claim 7, wherein automatically processing further comprises automatically causing, by the clinical messaging component, the health or patient records system to automatically update a patient record of the health or patient records system based on content of the clinical email message.

* * * * *